United States Patent [19]

Hegedus

[11] 4,449,394

[45] May 22, 1984

[54] EFFLUX VISCOSITY CUP

[75] Inventor: Allan J. Hegedus, Bolingbrook, Ill.

[73] Assignee: Mobil Oil Corporation, New York, N.Y.

[21] Appl. No.: 352,624

[22] Filed: Feb. 26, 1982

Related U.S. Application Data

[63] Continuation-in-part of Ser. No. 327,547, Dec. 4, 1981, Pat. No. 4,400,973.

[51] Int. Cl.³ ............................................. G01N 11/04
[52] U.S. Cl. ........................................................ 73/55
[58] Field of Search ...................................... 73/55, 56

[56] References Cited

U.S. PATENT DOCUMENTS

| | | | |
|---|---|---|---|
| 1,502,118 | 7/1924 | Osborne | 73/56 |
| 2,092,223 | 9/1937 | Payne | 73/55 |
| 2,141,329 | 12/1938 | Zahn | 73/56 |
| 2,564,892 | 8/1951 | Gerin | 73/56 |
| 2,743,605 | 5/1956 | Gamlen | 73/55 |
| 2,836,975 | 6/1958 | Euverard | 73/55 |

FOREIGN PATENT DOCUMENTS

211144  4/1968  U.S.S.R. ................................. 73/55

*Primary Examiner*—Gerald Goldberg
*Assistant Examiner*—Joseph W. Roskos
*Attorney, Agent, or Firm*—Alexander J. McKillop; Michael G. Gilman; Speciale, Charles J.

[57] ABSTRACT

This invention provides a rugged dip-type viscometer suitable for use in a rotogravure printing plant, for example. The capillary of the viscometer is joined to a protective collar and gives high precision measurements with inks that contain air. The protective collar is provided with one or more apertures to provide increased precision.

9 Claims, 16 Drawing Figures

EFFLUX VISCOSITY CUP

CROSS-REFERENCE TO RELATED APPLICATIONS

This application is a continuation-in-part of U.S. application Ser. No. 327,547, filed Dec. 4, 1981, now U.S. Pat. No. 4,400,973, the entire content of which is incorporated herein by reference.

BACKGROUND OF THE INVENTION

1. Field of the Invention

This invention is concerned with an improved diptype efflux viscosity cup. The improved cup is particularly useful for controlling the viscosity of rotogravure printing inks in the pressroom and for checking the calibration of automatic viscosity controls.

2. Prior Art

A large number of viscometers have been proposed and are in use for measuring the viscosity of paints, varnishes, lacquers, gravures and flexographic printing inks, and of other fluid products such as adhesives and petroleum oils. A relatively inexpensive and relatively durable type of viscometer which is well adapted to plant use is the diptype efflux cup, exemplified by the well known Zahn cup, and the equally well known Shell cup. The Zahn cup is described, for example, on page 1349 of the Sargent-Welch Catalog of Scientific Laboratory Instruments, and on page 1271 of the 1981 Fisher Scientific Catalog. This cup consists essentially of a cylindrical cup with a hemispherical bottom and has a nominal volume of about 44 ml and, concentric with the cylindrical axis, an orifice which varies from about 80 to about 210 thousandths of an inch, permitting a range of measurement of about 14 to about 13 hundred centipoises. The cup is provided with a long, looped handle and holding ring and it may be provided also with a thermometer. One of the disadvantages of the cup is that the orifice generally has no protection from accidental mechanical damage, for example, and therefore is subject to change in calibration.

In use, the Zahn cup is chosen having an orifice such that the liquid to be tested has an efflux time of less than about one minute. The cup is immersed in the liquid to be tested, and the viscosity is measured by raising the cup out of the liquid and determining the length of time required for the stream to break.

The Shell cup is similar to the Zahn cup except that it utilizes a capillary tube normally protected by a lip and construction integrally with the body of the cup. It is altogether somewhat more rugged, but the protecting lip may result in the entrapment of dirt or minute air bubbles and cause distortion of the flow pattern from the capillary and create reproducibility problems.

A modification of the Shell cup, which will be referred to herein as the "S cup", provides a protective collar around the orifice which extends about 2 (two) mm beyond the orifice of the capillary. With the S-cup, the orifice has the same diameter as the capillary itself, i.e., there is no lip around the orifice. Unlike the usual Shell and Zahn cups, the S-cup is free-standing and may be stored on a shelf or table without damage to the exit orifice of the capillary.

The present invention was motivated by repeated complaints from the pressroom of a rotogravure plant concerning the inability to achieve gool light end printout and maintain solid color density.

It is known that one of the most vital characteristics of a gravure ink, with respect to its performance, is the viscosity at which it is printed. Optimum press viscosity insures consistent quality results in the areas of printability, trapping efficiency, level of gloss, adhesion, color density and drying speed—to mention a few of the most important. Experience in the pressroom indicated that good printability on a coated stock red can be achieved by maintaining the viscosity of the ink between 29 and 28 seconds on a Zahn-1 cup.

A preliminary study of the viscosity control problem indicated that the Zahn cup lacked adequate sensitivity for good control. The S-cup, which is a modified Shell cup, appeared best suited in design and in sensitivity to measure the viscosity of rotogravure inks in the region in question. However, it was noted that the S-cup suffered from excessive scatter of data points.

It is an object of this invention to provide an improved efflux viscosity cup which is rugged in design, well adapted to routine production control in a plant environment, and which offers a combination of good sensitivity and good repeatability from test to test.

SUMMARY OF THE INVENTION

This invention is best summarized by describing the preferred embodiment. The efflux viscosity cup of this invention, designated herein as the "H-cup", is of basically the same design and dimensions as the S-cup of the prior art except for the provision of a pair of slots or arches cut in the protective collar with the tops of the slots or arches located at or slightly above the land bridging the capillary and the collar.

BRIEF DESCRIPTION OF THE DRAWING

| | |
|---|---|
| Fig. 1A | Side view of H-cup |
| Fig. 1B | View from above og H-cup |
| Fig. 1C | View from below of H-cup |
| Fig. 1D | Bottom view of H-cup |
| Fig. 2 | Cross section of H-cup |
| Fig. 3 | Comparison of Zahn and H-cup |
| Fig. 4 | Comparison of Zahn and H-cup |
| Fig. 5 | Comparisons with Coated Yellow |
| Fig. 6 | Comparisons with Coated Red |
| Fig. 7 | Comparisons with Coated Blue |
| Fig. 8 | Comparisons with Coated Black |
| Fig. 9A | Slots parallel to capillary bottom view |
| Fig. 9B | Vertical section of 9A |
| Fig. 9C | Slots perpendicular to capillary, bottom view |
| Fig. 9D | Side view of 9C |
| Fig. 9E | Vertical section of 9C |

DETAILED DESCRIPTION

Figures 1A, 1B, 1C, 1D:
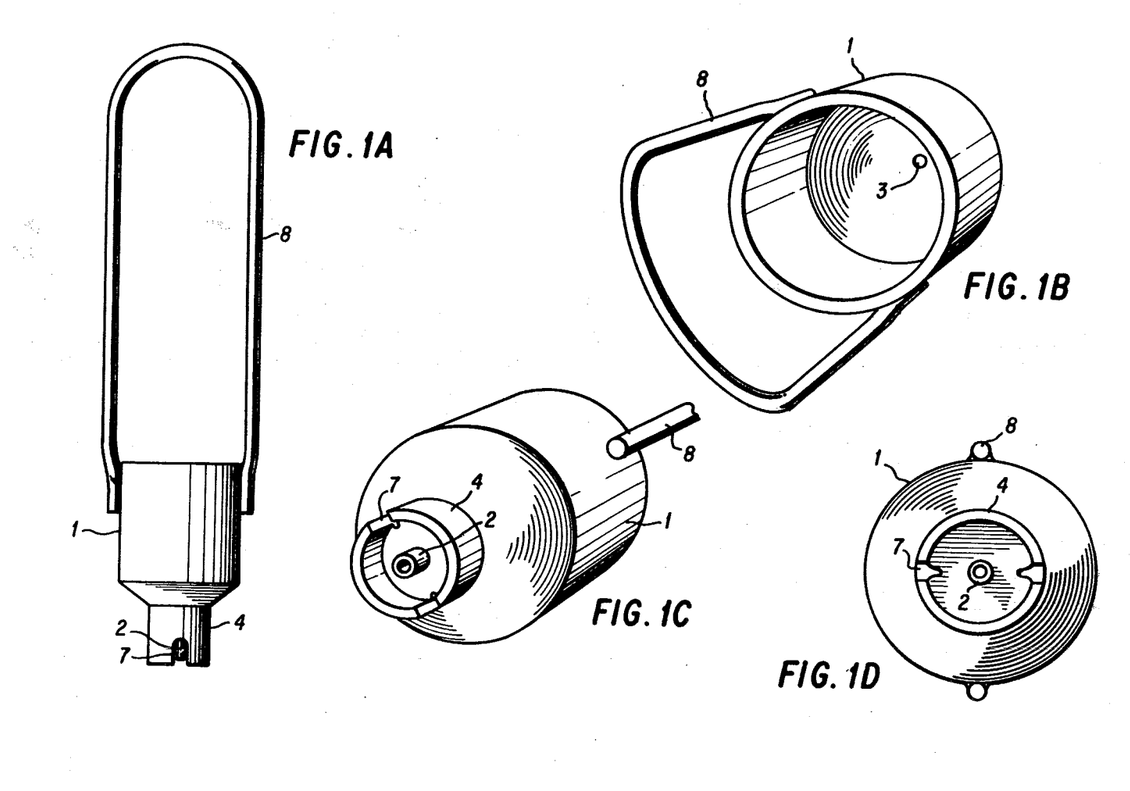

FIG. 1 of the drawing shows several perspective views of the H-cup.

Figure 2:
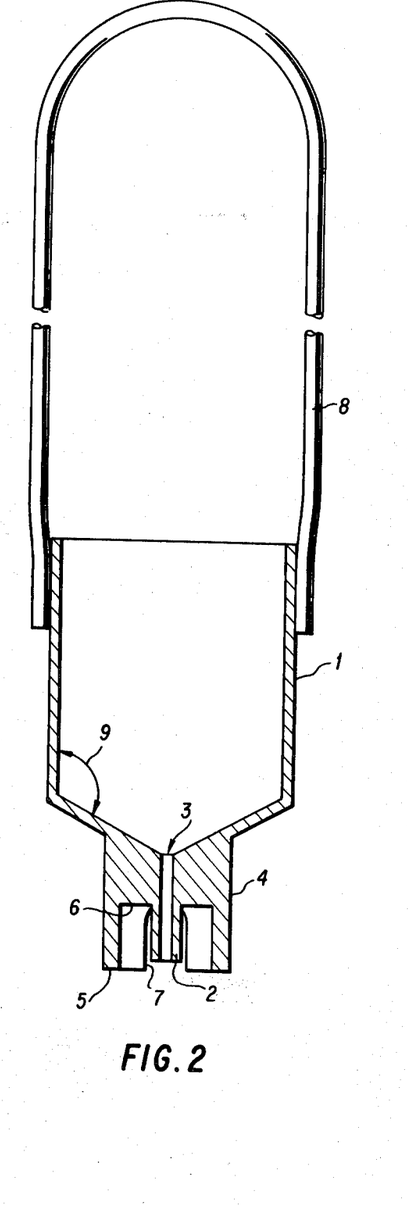

FIG. 2 of the drawing shows a cross-section of the H-cup and illustrates the overall unitized construction which is the preferred embodiment for purposes of this invention. The entire structure preferably is formed from a single block of stainless steel except for the handle which may be welded to the cup. The cylindrical cup with a conical bottom (1) joined to capillary (2) at the apex of the cup constitutes the basic viscometer. With unitized construction, the bore (3) of the capillary is initially made undersized, the cup tested, and then the capillary is rebored to exact size. The protective collar (4) is machined such that its inner diameter is about ⅜ inch to about one inch larger than the outer diameter of the capillary (2) and extends beyond the end of the capillary about 2 millimeters, thus protecting the capillary from mechanical damage and providing a base (5) for free-standing storage. The collar (4) is joined to the capillary (2) by a land (6) which is essentially parallel with the plane of the base (5). Two slots (7) extending from the base (5) at least to the land (6) are provided in collar (4). The slots may take the form of arches, as shown. The slots have a width of about ⅛ inch to ¼ inch. The angle (9) at the junction of the cone and cylinder may vary, but preferably is in the range of about 120° to about 140°. While not wishing to be bound by theory, it is believed that the slots improve reproducibility by facilitating the disengagement of air. The cup is fitted with handle (8).

Figure 3:
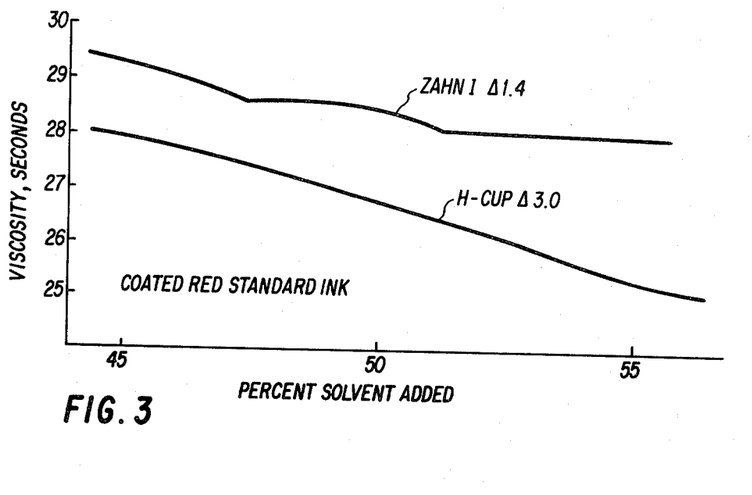

FIG. 3 illustrates the reduction of viscosity as measured by the Zahn-1 cup as a rotogravure ink is let down into the region of 28–29.4 seconds Zahn-1 viscosity. In this instance and all others shown herein, the percent solvent added is computed from:

$$\frac{\text{milliliters of solvent}}{\text{grams of ink + milliliters of solvent}} \times 100$$

It will be noted that the sensitivity of the Zahn cup falls off rapidly after an addition of about 47.5% solvent. The designation "coated red standard ink", etc., means a standard red for coated stock.

Figure 4:
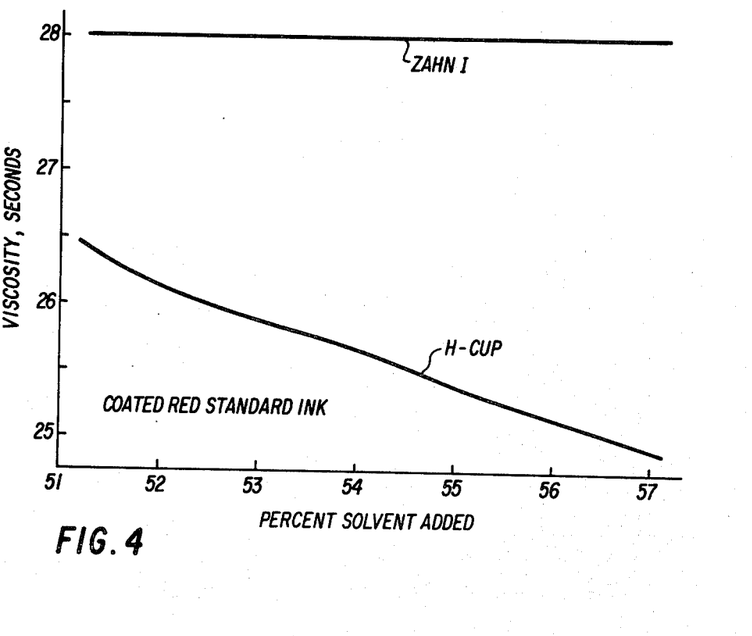
Figure 5:
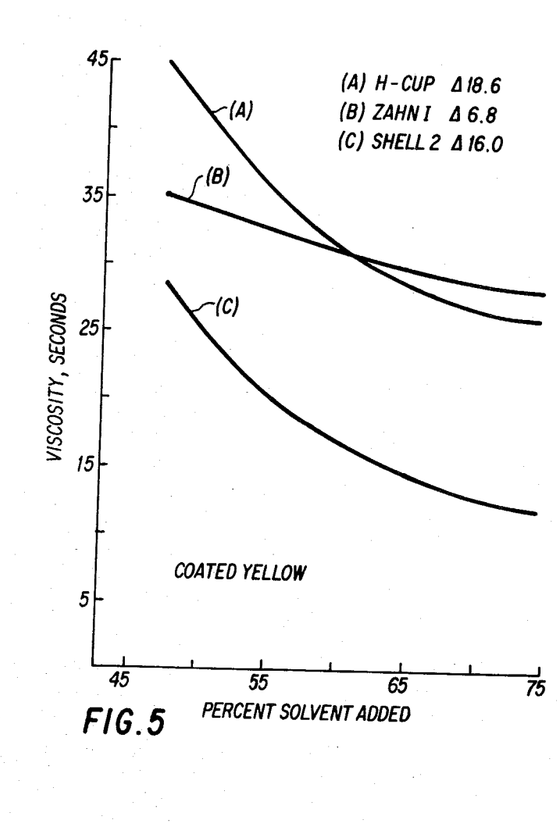
Figure 6:
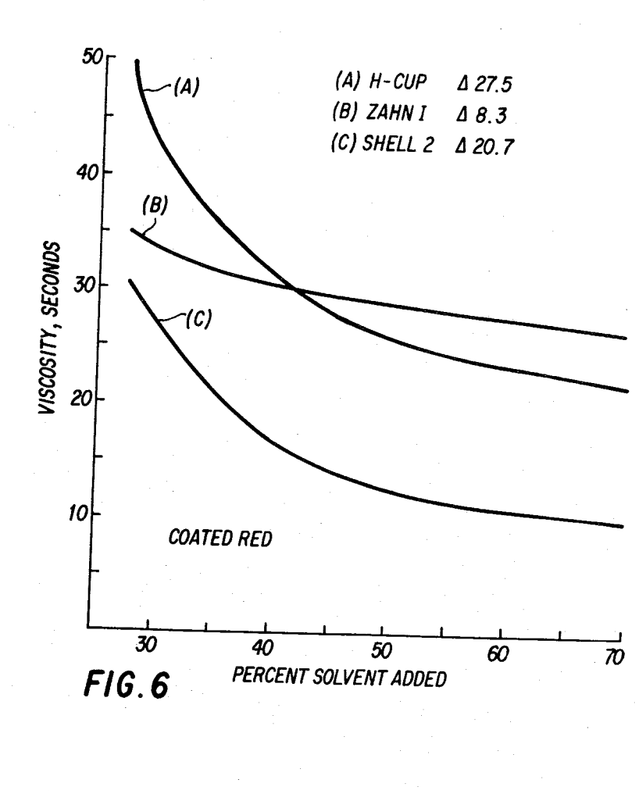
Figure 7:
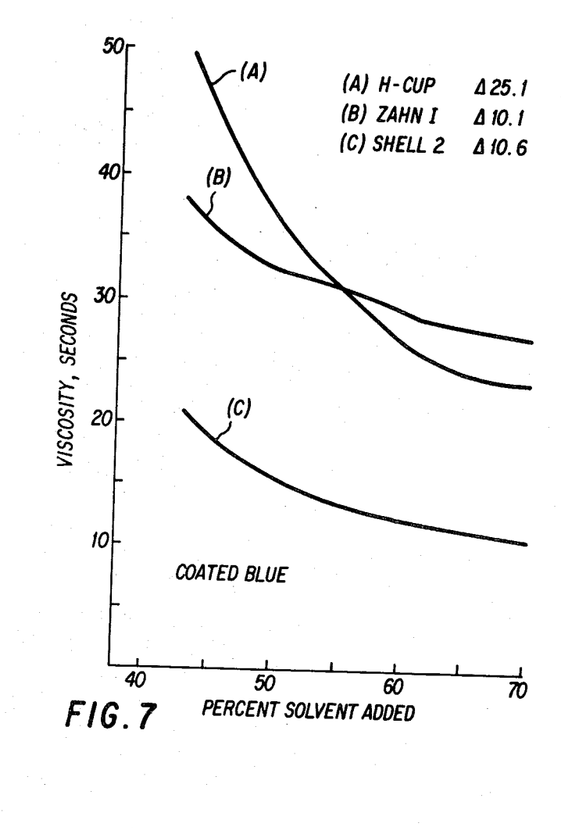
Figure 8:
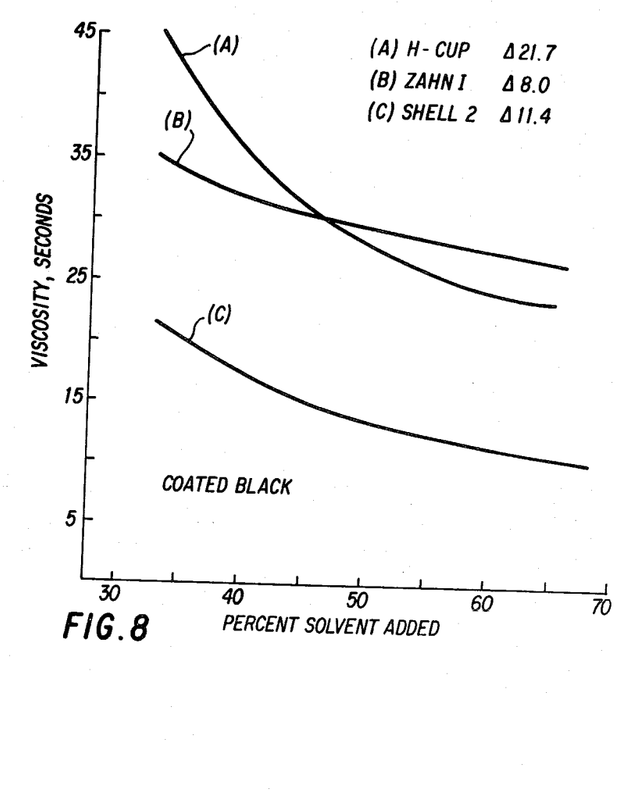
Figure 9A:
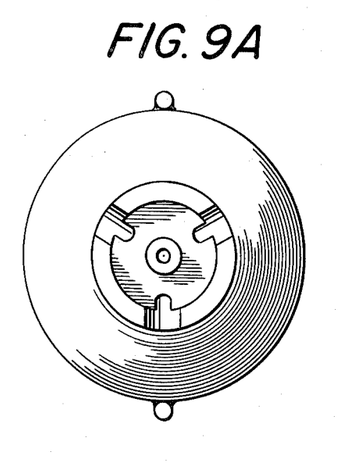
Figure 9B:
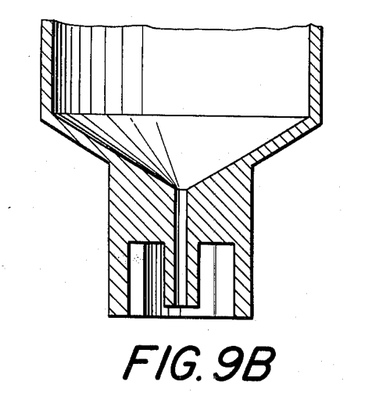
Figure 9C:
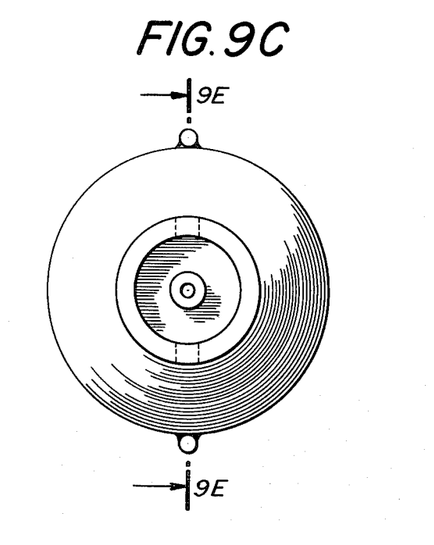
Figure 9D:
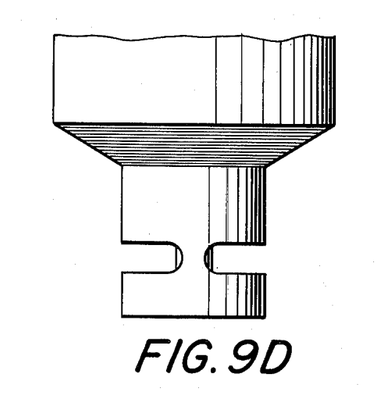
Figure 9E:
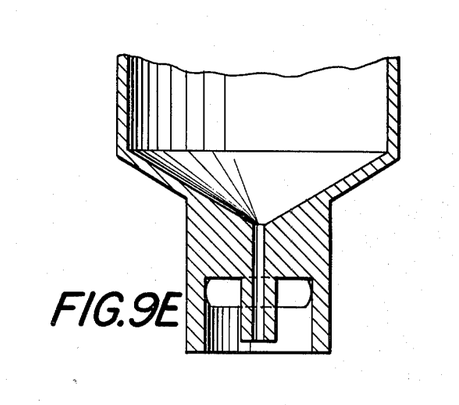

FIG. 4 compares the behavior of the Zahn-1 viscosity with the H-cup behavior over the region covered by the addition of 51–57% solvent. It is noteworthy that the Zahn cup is completely insensitive in this region giving a viscosity of about 28 seconds regardless of the dilution, whereas the H-cup responds with a change of about 1.5 seconds over the range.

FIGS. 5, 6, 7 and 8 illustrate the comparative behavior of the H-cup, the Zahn-1 and the Shell-2 for dilution of a set of gravure inks for application on coated stocks. In all cases, the H-cup maintains its sensitivity over a wide range of dilutions, and the Zahn cup is much less sensitive. The Shell cup is reasonably sensitive, as would be expected from its capillary element, but in all cases the H-cup gives the largest total differences from the lowest to the highest dilutions.

The physical characteristics and measurements of the cups used in the above tests are given in Table I. The somewhat larger capillary compared with the Shell cup reduces the chance for error from small particles of dirt.

TABLE I

PHYSICAL CHARACTERISTICS AND APPROXIMATE MEASUREMENTS

|  | H-CUP | S-CUP | ZAHN-1 | SHELL-2 |
|---|---|---|---|---|
| Weight (g.) | 318.5 | 274 | 103 | 144 |
| Volume (ml) 75° F. | 110 | 110 | 46 | 23 |
| Capillary Length (mm) | 21 | 21 | 0 | 25 |
| Orifice Diameter (mm) | 3 | 3 | 1.5 | 2 |

Table II shows the viscosity of different pure liquids in the four cups referred to.

TABLE II

VISCOSITIES OF DIFFERENT PURE SOLVENTS (Seconds)

|  | H-CUP | S-CUP | ZAHN-1 | SHELL-2 |
|---|---|---|---|---|
| Xylene 72° F. | 20.7 | 20.5 | 27.2 | 8.6 |
| Water 72° F. | 22.0 | 22.2 | — | 10.0 |
| Rotosolv 2271 72° F. | 21.5 | 21.0 | 28.0 | 8.5 |

Table III shows the variations of viscosity of a red rotogravure ink as temperatures change with the four cups under study.

TABLE III

VISCOSITIES (Secs.) AT VARYING TEMPERATURES, RED GRAVURE INK

| TEMPERATURE | H-CUP | S-CUP | ZAHN-1 | SHELL-2 |
|---|---|---|---|---|
| 42° F. | 45.2 | 45.0 | 33.8 | 27.5 |
| 72° F. | 35.7 | 35.0 | 31.0 | 19.4 |
| 104° F. | 30.0 | 30.0 | 29.3 | 15.0 |

As would be expected from the similarity of construction and of dimensions, the foregoing tables reflect similar behavior for the S-cup of the prior art and the H-cup of this invention. However, a statistical study of repeatability based on 50 tests with each the S-cup and the H-cup showed a radical difference in precision. A blend of mineral seal oils free of solvent and having a viscosity of 10 centipoises was used for these tests. The results of these tests, shown in Table IV, illustrates a marked superiority of the H-cup as compared with the S-cup.

TABLE IV

| | REPEATABILITY | |
|---|---|---|
|  | H-CUP | S-CUP |
| Value of Mean | 32.48 | 31.65 |
| Standard Deviation | 0.102 | 0.313 |

While the present invention has been described with particular attention given to the application of the improved cup of this invention to the measurement of the viscosity of gravure ink in a printing plant environment, it will be recognized that the advantages provided will be equally applicable to the measurement of paints, lacquers, and other liquids which require monitoring of viscosity under adverse conditions. Also, whereas the present cup has been described in a form suitable for measuring the viscosity of liquids in the range of those that would be measured by a Shell-2 cup, it is well evident that a set of cups with applicability over a range of viscosity comparable with different Shell cups is provided simply by changing the size of the capillary bore.

EQUIVALENTS

This invention has been described up to this point with particular reference to the preferred embodiment illustrated by FIGS. 1 and 2 of the drawing. A very important element of this embodiment is the pair of slots (7) located in the collar as shown in the drawing. These slots, capped by arches, are believed to be responsible for the large reduction in the standard deviation observed when comparable measurements are made with and without the slots, as illustrated by Table IV.

A number of variants of the preferred embodiment are contemplated. Some of these employ apertures other than those shown in the preferred embodiment, and others relate to different modes of construction of the viscosity cup. These will be discussed in turn.

In general, any viscosity cup in which a resevoir is joined to a capillary and in which the capillary has a protective collar with one or more apertures of a size and shape such that a substantial reduction of the standard deviation of measurements made with said viscometer is obtained when compared with the same viscometer without the apertures is contemplated as within the scope of this invention. It is believed that the design and location of the apertures which breach the protective collar are very important in determining the improvement obtained in the standard deviations. For purposes of the present invention, a reduction of the standard deviation to a value not larger than three quarters of the value obtained in the absence of apertures is considered substantial and characterizes the apertures as being effective. In some instances, as illustrated in the preferred embodiment of this invention, it is possible to reduce the standard deviation to a value not more than about half of what is obtained without the apertures. When this can be obtained without undue sacrifice of protection for the exit orifice of the capillary tip, it is desirable to design the apertures to provide such reduction.

Whenever standard deviation is referred to herein or in the claims, it refers to the standard deviation measured substantially as described.

Apertures which breach the protective collar may be holes of sufficient size and number to produce the desired effect. Or, they may be slots oriented in the protective collar in different ways. Slots such as are shown in FIGS. 1 and 2 of the drawing, and which have sides parallel to the capillary and a length about equal to the height of the collar are included within the scope of this invention. Such slots may breach not only the wall of the protective collar, but also its base. When two such slots are positioned about 180 degrees of arc apart on said collar, degrees of arc here being measured from center to center of each slot, it becomes evident that the capillary tip, in the line of sight of the slots, loses a small amount of protection. Placing the viscometer on a table that contains a rod-like foreign object, may cause the capillary to hit the rod-like object and undergo some distortion. This will be true for any slots or arches which are so placed that the capillary appears in the line of sight between said arches. This reduction in protective effect may be largely eliminated simply by locating the slots such that the capillary does not appear in the line of sight, as is the case when one separates two or three relatively narrow slots from each other by about 120 degrees of arc. In another variant, slots having sides parallel to the capillary and of a length somewhat shorter than the height of said collar are located in the uppermost part of the collar so that the base is not breached. In still another variant, slots which breach the base of the collar are cut with sides not parallel to the capillary and they are placed so that the capillary tip is not in the line of sight of the openings. In yet another variant of this invention, the slots are cut in the collar so that the sides of the slot are in a plane perpendicular of the capillary. With such slots the base is not breached at all, and full protection for the tip of the capillary is obtained even with the improvement of this invention. It should be noted that the effect of cutting two relatively long slots having sides perpendicular to the capillary is to provide a structure which may be characterized as a protective annulus for the capillary, which annulus is held in place by two post structures attached to the bottom of the cup or to some extension thereof. Such structures are within the scope of the invention regardless of how made, i.e. even if assembled from separate annulus and post elements.

Although the preferred embodiment described herein and illustrated by FIGS. 1 and 2 of the drawing describe the structure as made from a single block of metal, i.e. unitary, it is evident that other construction variants are within the scope of this invention. Any suitable cup-like resevoir may be used which is externally and communicatively joined at its bottom to a capillary in such a manner that the contents of the cup drain freely into the capillary. Different ways of joining the capillary to the cup may be used. For example, a threaded joint or a press-fitted joint may be used such that the capillary may be removed and replaced by a capillary of the same bore or of a different bore. The collar, likewise may be part of a unitary construction, or it may be a separate element made of one or more parts which are attached to the bottom of the cup by a threaded joint, by welding, by soldering, etc. Although the collar shown in FIG. 1 of the drawing is constructed as a cylindrical element, it need not necessarily be cylindrical but may take the shape of a frustrum of a cone for example. The diameter of the base of the cone in any case should be sufficiently large to provide, together with other design elements, a reasonable stability for the cup when it is in the free-standing state, such as when it is on a table top or placed in a carrier such as in a bucket containing solvent. The collar should not be so large however as to reduce excessively its protective action with reference to the exit orifice of the capillary. The base of the collar may be provided with a coarse screen to further protect the orifice. Although the preferred materials of construction for the cup are metals, particularly corrosion resistant metals such as stainless steel, it is conceivable that parts of the structure or all of it may be constructed of non-metallic materials. Regardless of the materials of construction, designs are preferred which have a low center of gravity, which of course enhances the stability of the cup in the free-standing state. To this end, excess metal may be provided in the bottom portion of the resevoir structure or in the upper portion of the collar structure, or both. All of the foregoing variants are contemplated as within the scope of the present invention.

FIG. 9 illustrates some of the variants described above. FIG. 9A illustrates three slots having sides parallel to the capillary and separated from one another by 120 degrees of arc. FIG. 9B is a cross-sectional view of FIG. 9A. FIGS. 9C and 9D represent views, and 9E the cross section, respectively, of apertures in the form of slots with sides in a plane perpendicular to the capillary. The tip of the capillary is well protected and not in the line of sight.

What is claimed is:

1. In an efflux viscosity cup consisting essentially of a cup-like resevoir externally and communicatively joined at its bottom to a capillary, a collar coaxially oriented with said capillary and attached at one open end to said bottom of said resevoir, said collar having an internal diameter substantially larger than the external diameter of said capillary and a height sufficient to extend it beyond the capillary thereby protecting the exit orifice of said capillary from damage, the improvement whereby increasing the accuracy of the viscometer, which comprises:

including one or more apertures in said collar, the size and location of said apertures being effective to substantially reduce the standard deviation of measurements made with said viscometer.

2. The article described in claim 1 wherein said aperture is a slot.

3. The article described in claim 1 wherein said aperture is a slot having sides parallel to said capillary and a length about equal to the height of said collar.

4. The article described in claim 3 having two said apertures separated from each other in said collar by about 180 degrees of arc.

5. The article described in claim 3 having three said apertures separated from one another in said collar by about 120 degrees of arc.

6. The article described in claim 1 wherein said aperture is a slot having sides perpendicular to said capillary.

7. The article described in claim 6 having two said apertures.

8. The article described in claim 1 wherein said one or more apertures are holes.

9. The article described in claim 1 or 2 or 3 or 4 or 5 or 6 or 7 or 8 wherein said one or more apertures are of such size and location as to reduce the standard deviation of measurements made with said viscometer to a value not more than about half of what is obtained without said apertures.

* * * * *